(12) United States Patent
Miquerol et al.

(10) Patent No.: US 7,399,902 B2
(45) Date of Patent: Jul. 15, 2008

(54) MOUSE CARDIAC CONDUCTION SYSTEM MODEL

(75) Inventors: Lucile Miquerol, Marseilles (FR); Daniel Gros, Marseilles (FR)

(73) Assignees: Centre National de la Recherche Scientifique (CNRS), Paris Cedex (FR); Universite de la Mediterranee (Aix-Marseille II), Marseilles (FR)

( * ) Notice: Subject to any disclaimer, the term of this patent is extended or adjusted under 35 U.S.C. 154(b) by 365 days.

(21) Appl. No.: 10/825,687

(22) Filed: Apr. 16, 2004

(65) Prior Publication Data

US 2006/0168674 A1 Jul. 27, 2006

Related U.S. Application Data

(60) Provisional application No. 60/463,057, filed on Apr. 16, 2003.

(51) Int. Cl.
*A01K 67/027* (2006.01)
*A01K 67/033* (2006.01)

(52) U.S. Cl. .............................. 800/18; 800/13; 800/14

(58) Field of Classification Search .................. None
See application file for complete search history.

(56) References Cited

OTHER PUBLICATIONS

Anumonwo, Justus M.B., et al., "Action Potential Characteristics and Arrhythmogenic Properties of the Cardiac Conduction System of the Murine Heart", Circulation Research, Aug. 17, 2001, pp. 329-335, 2001 American Heart Association Inc., USA.

Gourdie, Robert G., et al., "Development of Cardiac Pacemaking and Conduction System Lineages", Molecular Basis of Cardiovascular Disease, 2nd Edition, (ed. KR Chien), pp. 1-47, USA.
Jay, Patrick Y., et al., "Nkx2-5 mutation causes anatomic hypoplasia of the cardiac conduction system", The Journal of Clinical Investigation, vol. 113, No. 8, Apr. 2004, pp. 1130-1137, Ann Arbor, Michigan, USA, doi:10.1172/JCI200419846.
Meysen, Sonia, et al., "Nkx2.5 cell-autonomous gene function is required for the postnatal formation of the peripheral ventricular conduction system", Development Biology (2007), doi:1016/j.ydbio.2006.12.044.
Miquerol, Lucile et al., "Architectural and functional asymmetry of the His-Purkinje system of the murine heart", Cardiovascular Research 63 (2004), pp. 77-86, 2004 European Society of Cardiology, Elsevier B.V., Netherlands, doi:10.1016/j.cardiores.2004.03.007.
Myers, Dina C., et al., "Toward an Understanding of the Genetics of Murine Cardiac Pacemaking and Conduction System Development", The Anatomical Record Part A, 280A:1018-1021 (2004), 2004 Wiley-Liss Inc., Wilmington, Delaware, USA, doi:10.1002/ar.a.20077.
Nguyen-Tran, Van T.B., et al., "A Novel Genetic Pathway for Sudden Cardiac Death via Defects in the Transition between Ventricular and Conduction System Cell Lineages", Cell, vol. 102, pp. 671-682, Sep. 1, 2000, 2000 Cell Press, Cambridge, MA, USA.
Pashmforoush, Mohammad, et al., "Nkx2-5 Pathways and Congenital Heart Disease: Loss of Complete Heart Block", Cell, vol. 117, 373-386, Apr. 30, 2004, 2004 Cell Press, Cambridge, MA, USA.

*Primary Examiner*—Peter Paras, Jr.
(74) *Attorney, Agent, or Firm*—Arent Fox LLP

(57) ABSTRACT

The present invention relates to a transgenic mouse which has integrated a reporter gene in the locus of the Cx40 gene, wherein said reporter gene is expressed in the different components of the cardiac conduction system (CCS) including the atrio-ventricular node (AVN). His bundle, bundle branches and Purkinje fibers.

Figure 1A:
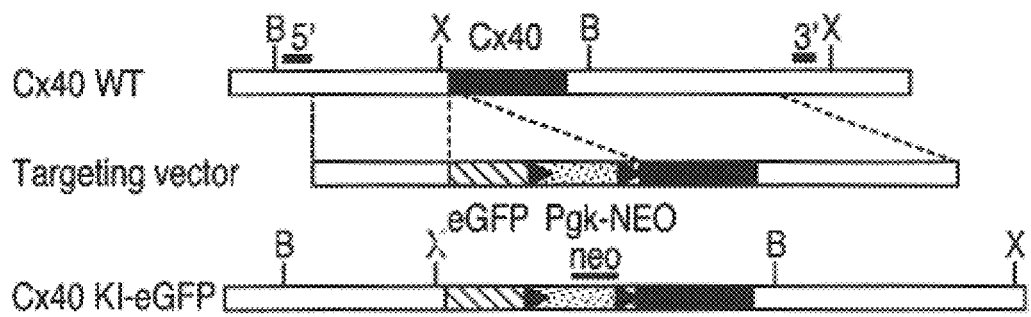
Figure 1B:
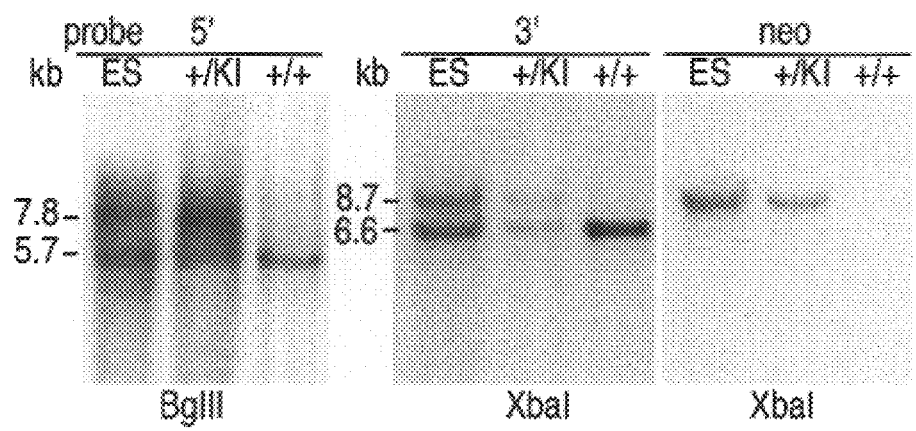

4 Claims, 10 Drawing Sheets
(7 of 10 Drawing Sheet(s) Filed in Color)

| | VM | RBB | LW |
|---|---|---|---|
| RMP | -75.18 ± 2.53 | -75.45 ± 1.54 | -75.33 ± 1.18 |
| APA, mV | 86.83 ± 2.16 | 82.33 ± 3.04 | 91.05 ± 0.76* |
| APD50, ms | 8.53 ± 0.78 | 9.11 ± 0.41 | 13.35 ± 0.61* |
| APD70, ms | 18.88 ± 2.39* | 26.27 ± 2.87* | 39.47 ± 3.04* |
| APD90, ms | 58.73 ± 6.18* | 82.55 ± 3.75* | 78.74 ± 4.91 |

MOUSE CARDIAC CONDUCTION SYSTEM MODEL

This application claims the benefit of Provisional Application No. 60/463,057 filed Apr. 16, 2003. The entire contents of the above-identified application is incorporated by reference.

The invention pertains to the field of biology and genetic manipulation in isolated cells or in living organisms to produce transgenic non-human animal models for testing compounds useful for treating various pathologies. More specifically, the invention relates a transgenic mouse which has integrated a reporter gene in the locus of the Cx40 gene, wherein said reporter gene is expressed in the different components of the cardiac conduction system (CCS) including in the atrio-ventricular node (AVN), His bundle, bundle branches and Purkinje fibers.

BACKGROUND OF THE INVENTION

Cardiovascular diseases represent the first cause of mortality in our modern societies. Troubles in the conduction of the electrical activity through the heart are frequently observed in these pathologies and they could lead to arrhythmias underlying the direct cause of death (Zipes and Wellens, 1998). The Purkinje conduction system is also in involved in ventricular fibrillation representing the main mechanism of cardiac sudden death in human (Haissaguerre et al, 2002). Multiples causes such as genetic and environmental factors have been advanced to explain the high incidence of arrhythmias and several genes responsible for familial diseases have already been discovered (review, (Roberts and Bragada, 2003).

Pumping function of the heart depends on the well coordination of cardiac contractions that are triggered by a depolarizing electrical activity. The cardiac conduction system (CCS), mediates the propagation of this electrical impulse through the different cardiac compartments. The different components of the CCS are well described in mammals and distinguishable by anatomic, histologic and electrophysiological features (Davies et al, 1983; Massing and James, 1976; Schram et al., 2002; Viragh and Challice, 1977b). The sinoatrial node (SAN), localized in the right atrium, is responsible for the pacemaker function of the heart (Boyett et al., 2000). From this node, the impulse spreads through the atria and reaches the atrio-ventricular node (AVN). After a small delay, the impulse is then transferred to the ventricles through a specialized conductive system, which comprises the his bundle, the bundle branches (BB) and the Purkinje fibers (Pt). The gap junctions (GJs) ensure the electrical coupling between cardiomyocytes by connecting cytoplasms of two adjacent cells. The GJs are aggregates of intercellular channels formed by transmembrane proteins belonging to the connexin family (Cx) (Review, (Gros and Jongsma. 1996; van Rijen et al., 2001).

The structure and function of the CCS have extensively studied in big mammals (dog, rabbit, bovine) because this specialized tissue can be easily isolated from the compact layer of the heart (Davies et al. 1983). Nevertheless, the murine CCS is poorly characterized because of the impossibility to visualize these cells from the surrounding ventricular myocardium. As a result, there is no mouse CSS model available as of today.

However, there a great need for a mouse model since disturbances in the CCS leads to arrhythmias which may lead to sudden death as well as other cardiac medical conditions.

Few decades ago, it has been shown that the murine cardiac conductive cells can be recognized from the working myocytes by histological differences with electronic microscopy procedures (Viragh and Challice, 1 977a; Viragh and Challice, I 977b). However, this specialized tissue is undistinguishable from the ventricular wall when the ventricular cavities are exposed under a stereomicroscope. The detection of the CCS and electrophysiological measurements are not directly possible in mouse models stained for ACTH (Anumonwo et al., 2001) or in the CCS-LacZ transgenic mice expressing LacZ reporter gene in the developing cardiac conduction system (Rentschler et al., 2001). In both cases, the revelation of the CCS was done after fixation of the tissues that render impossible direct electrophysiological analyses.

Therefore, it is necessary to design alternative models that would allow such analysis. In this regard, we obtained transgenic mice expressing a reporter protein specifically in the CCS tissue which circumvent the above mentioned problems. This has been possible by targeting the connexin-40 (Cx40) locus.

In mammals, the connexin-40 (Cx40) is expressed in cardiomyocytes and vascular endothelial cells. In the heart, Cx40 is restricted to the atria and to the ventricular conduction system (AVN, His bundle, bundle branches and Purkinje fibers) and is not expressed in ventricular contractile myocytes (Coppen and Severs, 2002; Delorme et al., 1997; Delorme et al., 1995). In mice lacking the Cx40 gene, abnormal ECGs have been recorded and are associated with conduction defects in the right and left BB (Bevilacqua et al. 2000; Kirchhoff et al., 1998; Simon et al., 1998; Tamaddon et al., 2000; van Rijen et al., 2001).

We have generated transgenic mice in which the vital marker eGFP is expressed in the entire ventricular conduction system by knock-in the GFP gene at the Connexin 40 locus. eGFP is detected in the different components of the CCS such as the AVN, His bundle, bundle branches and Purkinje fibers. We have shown that eGFP cells present electrical features of conductive cardiomyocytes and that the anatomical description of the left and right bundle branches are correlated with their respective electrical activity maps recorded. These data give an accurate image of the entire mouse ventricular conduction system.

Our results show that the anatomical asymmetry observed between the right and left 1313 with GFP expression corresponds to a physiological reality as it is proven by the activation maps recorded for each branch. So, the propagation of the electrical activity follows the anatomic roads forming by the RBB and LBB revealed in GFP. These data confirm the hypothesis that the morphological discrepancy observed between the thin RBB and the large LBB may explain the occurrence of RBB block in Cx40 knockout mice while only slowing propagation was observed in the left branch (Tamaddon et al., 2000; van Rijen et al., 2001). It is noteworthy that in human patients a higher susceptibilty to develop RBB block than LBB block (Dorman et al., 2000).

Such a precise anatomic picture of the murine conductive tissue was never given before in the literature. These images of the murine CCS are identical to those given for the human heart a century ago, demonstrating a perfect conservation of this anatomic structure between the mouse and the big mammals (Tawara, 1906). We have shown that the morphology of the CCS fits perfectly with the propagation of the electrical activity in the heart.

So, we found that a structure function relationship exists between the GFP images and electrical activation maps.

The GFP is a powerful tool in molecular and cell biology (Hadjantonakis et al., 2002). The main advantage of using this reporter gene in our KI Cx40/GFP mouse model comes from the fact that this protein can he easily detectable on living tissues and cells. Therefore, the Cx40/GFP mice of the invention represent the first model in which this tissue is directly visualized on fresh tissue. This is a tremendous progress for performing electrophysiological studies of the mouse CCS as well as testing compounds which could be useful for preventing or treating various cardiac medical conditions.

DESCRIPTION

Therefore, in a first aspect, the invention relates to a transgenic mouse which has integrated a reporter gene in the locus of the Cx40 gene, wherein said reporter gene is expressed in the different components of the cardiac conduction system (CCS) including the atrio-ventricular node (AVN), 1-us bundle, bundle branches and Purkinje fibers.

The transgenic mice of the invention are capable of transmitting the knocked-in reporter gene to their offsprings.

The reporter gene of the invention can encode for a reporter protein selected in the group consisting of autofluorescent proteins and enzymes detectable by a histochemical process. The autofluorescent protein is selected in the group consisting of the green fluorescence protein (GFP), the enhanced green fluorescence protein (eGFP), the red fluorescence protein (RFP), the blue fluorescence protein (BFP), the yellow fluorescence protein (YFP) and the fluorescent variant of these proteins. The enzyme detectable by a histochemical process is selected in the group consisting of β-galactosidase, β-glucoronidase, alcaline phosphatase, luciferase, alcohol deshydrogenase, chloramphenicol-acetyl transferase, peroxydase. The substrates to be used with these specific enzymes are generally chosen for the production, upon hydrolysis by the corresponding enzyme, of a detectable color change. Substrate can be soluble or insoluble, added into the culture medium or in the organism, or present in the host cell, depending upon the chosen method. For example, 5-bromo-4-chloro-3-indoyl phosphate/nitroblue tetrazolium is suitable for use with alkaline phosphatase conjugates; for peroxidase conjugates, 1,2-phenylenediamine-5-aminosalicylic acid, 3,3,5,5,-tetramethylbenzidine, tolidine or dianisidine are commonly used.

Such mice may be obtained by preparing vectors comprising the coding sequence of the reporter protein, which vector is suitable for homologous recombination into the Cx40 gene locus or which has also integrated recombinase protein specific sites to also excision and insertion of said sequence into the Cx40 gene locus. Preferably mice ES cells which have integrated said reporter gene sequence are selected and implanted in mice embryos leading to adult mice expressing the transgene and ES cells have contributed to the formation of the germinal tissue.

The expression "recombinase protein" is understood to designate recombinases of the family of integrases which catalyze the excision, insertion, inversion or translocation of DNA fragments at the level of specific sites of recognition said recombinases (Steinberg et al., 1986; Sauer, et al., 1990; Barbonis et al., 1993; Kilby et al., 1993; Sauer, 1994; Denisen et al., 1995). These recombinases are active in animal cells (Sauer, 1994). The recombinase protein of the invention is preferably selected from the group of site-specific recombinases composed of the Cre recombinase of bacteriophage P1, the FLP recombinase of *Saccharomyces cerevisiae*, the R recombinase of *Zygosaccharomyces rouxii* pSR1, the A recombinase of *Kluyveromyces drosophilarium* pKD1, the A recombinase of *Kluyveromyces waltii* pKW1, the integrase λ Int, the recombinase of the GIN recombination system of the Mu phage, of the bacterial β recombinase (Diaz et al., 1999) or a variant thereof.

In a particular embodiment, a transgenic mouse of the invention which has integrated the eGFP gene in the locus of the Cx40 gene will be referred herein as $Cx40^{KIGFP/+}$.

In this $Cx40^{KIGFP/+}$ mouse, the Cx40 gene is active and the Cx40 protein is expressed and co-localized with the eGFP transgene.

The invention also relates to a mouse offspring resulting from the crossing of a mouse according as depicted above with a mouse of the same or different genetic background, wherein said mouse offspring is a double eGFP+ allele.

In addition, a $Cx40^{KIGFP/+}$ mouse may further comprise at least one allele which is inactivated.

Such mice as defined above are particularly useful as cardiac conduction system (CCS) model. For example, in a $Cx^{40KIGFP/+}$ mouse, the eGFP+ cells present electrical features of conductive cardiomyocytes and the anatomical description of the left and right bundle branches are correlated with their respective electrical activity maps recorded, providing an accurate image of the entire mouse ventricular conduction system. Therefore, the GFP images obtained after applying action potentials stimuli correspond to the electrical activation maps.

In a second aspect, the invention is aimed at a method for performing electrophysiological studies of the mouse CCS comprising applying an action potential stimuli to a mouse according to the invention and taking images of fluorescent tissues with a digital camera.

Alternatively, the method of the invention may consist of testing whether or not a compound is inducing cardiac arrhythmias comprising administering said compound to a mouse as defined above and taking images of fluorescent tissues with a digital camera.

Also, the method of the invention may consist of screening compounds capable of preventing or treating cardiac arrest comprising administering candidate compounds and inducing ventricular fibrillation to a mouse as described above, taking images of fluorescent tissues with a digital camera and selecting a subset of compounds for which cardiac protection is observed in said fluorescent images.

The invention also encompasses a method for screening compounds capable of preventing or treating a cardiovascular disease comprising administering candidate compounds and inducing the onset of said cardiovascular disease to a mouse as mentioned above, taking images of fluorescent tissues with a digital camera and selecting a subset of compounds for which cardiovascular disease protection or cure is observed in said fluorescent images.

These methods may further comprise an action potential recordings, an ECG recording and/or a septal mapping.

It will be referred to the figure legends in the detailed description below.

Figure Legends

This application contains ten (10) figures executed in color. Copies of this patent application with color drawings has been provided by Applicant with the required fees under 37 CFR §1.17(h).

FIG. 1: Generation and Molecular Characterization of KI cx40-GFP Mice.

Genomic structure of the Cx40 gene with a unique coding exon (black box). A targeting vector comprises 2.7 kb and 5.7 kb of Cx40 genomic sequences as 5' and 3 homology arms; the eGFP coding sequence (dashed box), is inserted in frame at the Cx40 start codon followed by a pgk-neo cassette (dotted box) flanked by two LoxP sites (black arrowheads). Probes for Southern-blot are represented by bold line on top of the Cx40 genomic representation (5', 3'), X, XbaI; B, BglII.

Identification of homologous recombinant allele KI Cx40-GFP by Southern-blots. DNA from recombinant ES cell clone (ES) and from wild type (+/+) and heterozygous Cx40+/GFP (+/KI) mouse tail were digested with BglII or XbaI and hybridized with two external probes 5' or 3', respectively. The unique insertion of the targeting vector was verified by hybridization of the XbaI digested DNA with the internal probe corresponding to the neo sequence (neo).

Transcriptional analysis by RT-PCR of RNA extracted from Cx40+/GFP atria. Primers Exon1 (Ex1) and Exon2 (Ex2) amplified a 380 bp band corresponding to the Cx40 wild type transcripts, whereas Ex1 and GFP primers produced a 450 bp fragment from KI Cx40-GFP allele.

```
                                            (SEQ ID No 1)
    Cx40Ex1    (5'-AGAGCAAATAACAGTGGGCAGTTGA-3')

(SEQ ID No 2)
    Cx40Ex2    (5'-ACCAGG-CTGAATGGTATCG-3')

(SEQ ID No 3)
    GFP        (5'-AGAAGTCGTGCTGCTTCATG-3').
```

Co-localization of Cx40 and GFP proteins in atrial cardiomyocytes. The right panel represent the bright field section of a CX40+/GFP mouse atrium. In the left panel, green fluorescent corresponds to the cytoplasmic expression of GFP in all atrial cardiomyocytes, and the red fluorescence corresponds to an immunostaining with an anti-Cx40 antibody.

FIG. 2: eGFP Expression in Adult Heart of Cx40GFP/-t-transgenic Mice

Unfixed adult whole heart exposed to a GFP excitation source and examined under dissecting microscope with the appropriate filters (Leica). GFP fluorescent is visible in both atria (a) and in coronary arteries (arrows).

Upper view of an adult heart after removal of the atria, GFP expression is localized in the His bundle at the summit of the interventricular septum (arrow).

GFP expression observed in the left ventricular cavity. The ventricular chamber was opened on one side to expose the left septum side and the ventricular free wall, these are approximately separated by a dotted line. GFP expression revealed the structure of the LBB and the left web of the Purkinje system. LBB, left bundle branch; Pf, Purkinje fibers.

GFP expression observed in the right ventricular cavity. The separation between the right side of the interventricular septum and the ventricular free wall is defined by a dotted line. GFP is detected in the RBB and Purkinje fibers. The septal artery is indicated by arrows. AVN, atrio ventricular node; HIS, common bundle; RBB, Right bundle branch.

(E-H) Frozen sections of paraformaldehyde pre-fixed adult heart observed under microscope with a green excitation light (488 nm) E: High power section of the sino-atrial node (SAN). GFP is observed in the crista terminalis (CT), and in endothelial cells of the nodal artery (arrow).

GFP expression in the His bundle (HIS) and in the left (LBB) and right (RBB) branches.

GFP expression in the atrio-ventricular node (AVN).

GFP expression in the Purkinje fibers found in subendocardial surface at the apex of the left ventricle.

Figure 3:
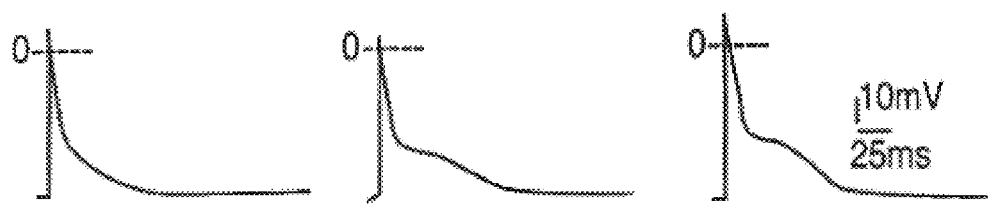

FIG. 3: eGFP Positive Cells Present Electrical Features of Conductive Cardiomyocytes Comparison of action potential parameters in the mouse ventricular myocardium GFP-(VM) and conductive cells GFP+ (RBB, LW). Action potentials were measured on opened heart using glass microelectrodes filled with 3 mol/L (resistance of 15 to 30M). The preparations were driven at pulse duration of 2 ms at 2 HZ. APs are recorded on whole opened heart under U.V. lighting. Values are mean+/− SEM, n=number of cells: RMP indicates resting membrane potential; APA, action potential amplitude: APD(50,70,90), action potential duration, respectively, at 50%, 70%, and 90% repolarization.

Representative AP recordings from VM, ventricular myocardium; RBB, the right bundle branch; LW, the left web.

FIG. 4: Impulse Propagation in the Bundle Branches of Cx40GFP/+ Mice in Sinus Rhythm Methods are as described previously (van Rijen et al. 2001; 103). Local electrograms arc shown taken from the indicated electrodes, and the specific bundle branch signal is marked by an asterisk. The large deflection represent activation of the septal working myocardium. Color codes represent local activation times (ins), relative to the remote atrial activation and are given for each panel separately.

Right bundle branch activation map; conduction velocity at 32 cm/s (average 33.8±1.4 cm/s; mean±SEM, N=4).

Left bundle branch activation map, conduction velocity at 40 cm/s (average 36.5±2.1 cm/s; mean+SEM, N=4). The average values are similar to those of wild type mice, i.e., 31 and 42 cm/s for RBB and LBB, respectively (van Rijen et al. 2001).

RBB represented by one fiber GFP+ descending from the His bundle (arrows). The red star indicates the position of the septal artery GFP+ that cross the RBB.

LBB is widely distributed on the left septal surface.

EXAMPLE 1

The KI Cx40/GFP Mouse Model

Material and Methods

Construction of the Targeting Vector

A fragment spanning about 12 kb of the locus of the Cx40 gene was isolated from the EMBL3 129Sv mouse genomic library. This fragment which included exon 2 (containing the complete coding sequence) flanked by a 4 kb region upstream, and a 8 kb region downstream, was mapped. A subfragment comprising 2.7 kb of 5 genomic sequence followed by the first 300 bp of the Cx40 exon 2 was cloned in pBluescript (Stratagene). An NcoI site (CCATGG) was created by PCR mutagenesis at the translation star site ( . . . AAGATGGGT . . . ) of the exon.

The eGFP sequences (NcoI-XhoI fragment, 1008 pb, from the pIRES-eGFP, Clonetech) was cloned in frame at the NcoI site of the Cx40 start codon. The neomycin selection marker, flanked by two identically orientated LoxP sites (LoxP-pgk-neo-LoxP) was then introduced after the GFP sequences. Finally, a 3'- homology genomic subfragment (5.7 kb) from the Cx40 locus, including the last 800 bp of exon 2, was inserted downstream the LoxP-NeoR-LoxP. The structure of this targeting vector, pCx40-KI/GFP is summarized in the FIG. 1A.

Generation of Knock-in Mice

R1 ES cells (129 SvJ/Svcp strain) were cultured and maintained in an undifferentiated state as previously described (Nagy et al., 1993). The pCX40-KI/GFP vector was linearized using Apa1 and electroporated (240 V. 500 µF) into ES cells. Genomic DNA prepared from 1500 G4 18-resistant clones (350 µg/mL), was digested with Xba1 and screened by Southern blot using a 3' external probe, 671 bp, localized downstream the 3' homology arm of the Cx40 gene (+5967 to +6638) (Hennemann et al., 1992). Correct targeting clones were further confirmed by BglII digestion and using a 5' external probe, 668 bp, upstream to the 5' Cx40 homology arm (−3325 to −2657) (Hennemann et al., 1992). A single integration of the targeting vector was subsequently verified by stripping and rehybridizing the XbaI-digested Southern blot with an internal neo probe, 720 bp.

Four independent recombinant ES cell clones, KI/Cx40-GFP, were injected into 3.5 dpc C57B1/6 blastocysts, then transferred to pseudopregnant CBA/C57B1/6 foster mothers. Chimeras were crossed with either CD-I mice or C57/B16 mice to generate either a 129Sv/CD1 genetic background, or a129Sv/C57B1/6 background.

Expression of the Transgene in the 1(1 Mice

RT-PCR experiments. Total RNA were extracted from the atria of heterozygous KI Cx40/GFP adult mice using TriZol reagent (GIBCO/BRL). 2 µg of RNA was reverse transcribed using First Strand cDNA Synthesis Kit (Roche Diagnostics). Samples were subjected to 30 cycles of PCR employing standard thermocycling conditions:

denaturation at 92°C. for 30 s, Annealing at 58°C. for 30 s and elongation at 72°C. for 1 min. Primers Exon1 (Ex1) and Exon2 (Ex2) amplified a 380 hp band corresponding to the Cx40 wild type transcripts, whereas Ex1 and GFP primers produced a 450 bp fragment from the KI Cx40/GFP allele.

Cx40ExI (5'-AGAGCAAATAACAGTGGGCAGTTGA-3') (SEQ ID No 1);

```
                                      (SEQ ID No 1)
Cx40ExI    (5'-AGAGCAAATAACAGTGGGCAGTTGA-3');

(SEQ ID No 2)
Cx40Ex2    (5'-ACCAGGCTGAATGGTAT-CG-3');

(SEQ ID No 3)
GFP        (5'-AGAAGTCGTGCTGCTTCATG-3').
```

Observation of Green Fluorescence

Adult mice were anesthetized and perfused in the dorsal aorta with phosphate-buffered-saline (PBS) to remove the excess of blood. The heart was isolated and examined in PBS under MZ10 stereomicroscope equipped with GFP excitation sources and appropriate filters (Leica GFP Plus fluorescence filter set). Images of fluorescent tissues were directly acquired with a digital camera (software Nikon ACT-1). For sectioning, adult tissues were fixed in freshly prepared 4% (wt/vol) paraformaldehyde solution at 40°C. for one hour, then washed in PBS, and incubated successively in 15% (wt/vol) and 30% (wt/vol) sucrose at 4°C. overnight. Tissues were embedded in OCT compound, frozen on dry ice and cryosectioned between 15 and 20 µm. Finally, sections were washed, mounted with Dabco-Mowiol and observed using a microscope equipped with a FITC filter (Zeiss).

Immunofluorescence Experiments

Cryosections were washed in PBS and then incubated with a saturation solution made with PBS containing 2% (wt/vol) BSA and 0.05% (wt/vol) saponin. The primary antibody diluted in the saturation solution was added for overnight incubation at 4°C. After washing, the sections were incubated with a secondary antibody for 1 hour at room temperature. After washing, sections were mounted in Dabco-Mowiol. Anti-Cx40 rabbit antibodies was used at 4 µg/mL (Gros et al., 1994). A Secondary antibodies used were Texas-Red conjugated donkey anti-rabbit IgGs (Jackson ImmunoResearch Lab.) diluted at 1:200.

Action Potential Recordings

Mice were anesthetized, hearts were excised and immersed in a standard solution containing (mM): NaCl, 130; $NaHCO_3$, 24; $NaHPO_4$, 1.2; KCl, 4; $CaCl_2$, 1.8; $MgCl_2$, 1; glucose, 11; saturated with 95%$O_2$ and 5% $CO_2$ at 36° C. (pH=7.4). After removal of the atria, the left ventricle was opened to expose the conduction system which can be visualized by fluorescence light microscopy. The preparations were pinned to the bottom of a 10 ml organ bath and superfused continuously with standard solution at the rate of 2 ml/min. Transmembrane potentials were recorded by conventional glass microelectrodes filled with 3 mol/L KCl (resistance of 15 to 30 M). The preparations were driven at pulse duration of 2 ms at 2 HZ. Actions potentials were digitized and analyzed with Pclamp6 5Axon Instruments Union city, Calif., USA) and Origin Softwares (Microcal Software, Northampton, USA).

ECG Recording and Septal Mapping

After anesthesia (urethane 2 g/kg body weight), standard 3-lead EGG recordings were performed, digitized at 2 kJIz and stored for off-line analysis. Subsequently, the hearts were excorporated, connected to a Langendorff setup and extracellular epicardial electrograms were recorded during sinus rhythm (SR) as previously described (van Rijen et al., 2001; van Veen et al., 2002). For mapping of the bundle branches, the right and left ventricular free walls. The 13×19 electrode grid (electrode spacing 300 pm; frequency, 4 kHz) was positioned on the septum and recordings were carried out in SR. Activation maps were constructed from activation times using custom.-written software (Potse et al., 2002). Maximal negative dV/dt in the unipolar electrograms was selected as the time of local activation. Maximum conduction velocities were determined by hand from the activation maps constructed from paced electrograms during basic stimulation.

Results

Figure 1C:
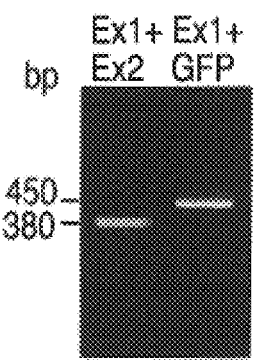
Figure 1D:
Figure 1E:
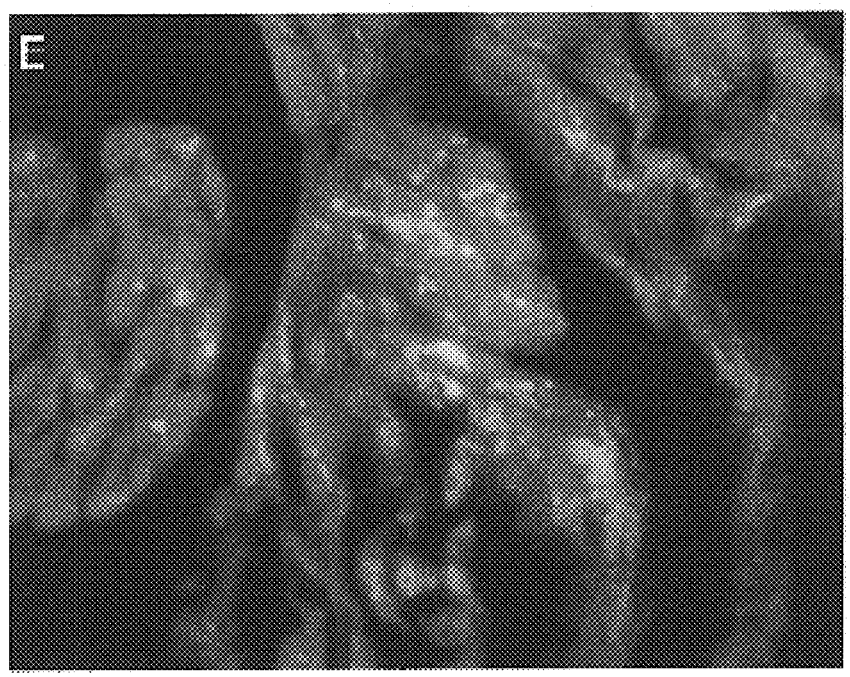
Figure 2A:
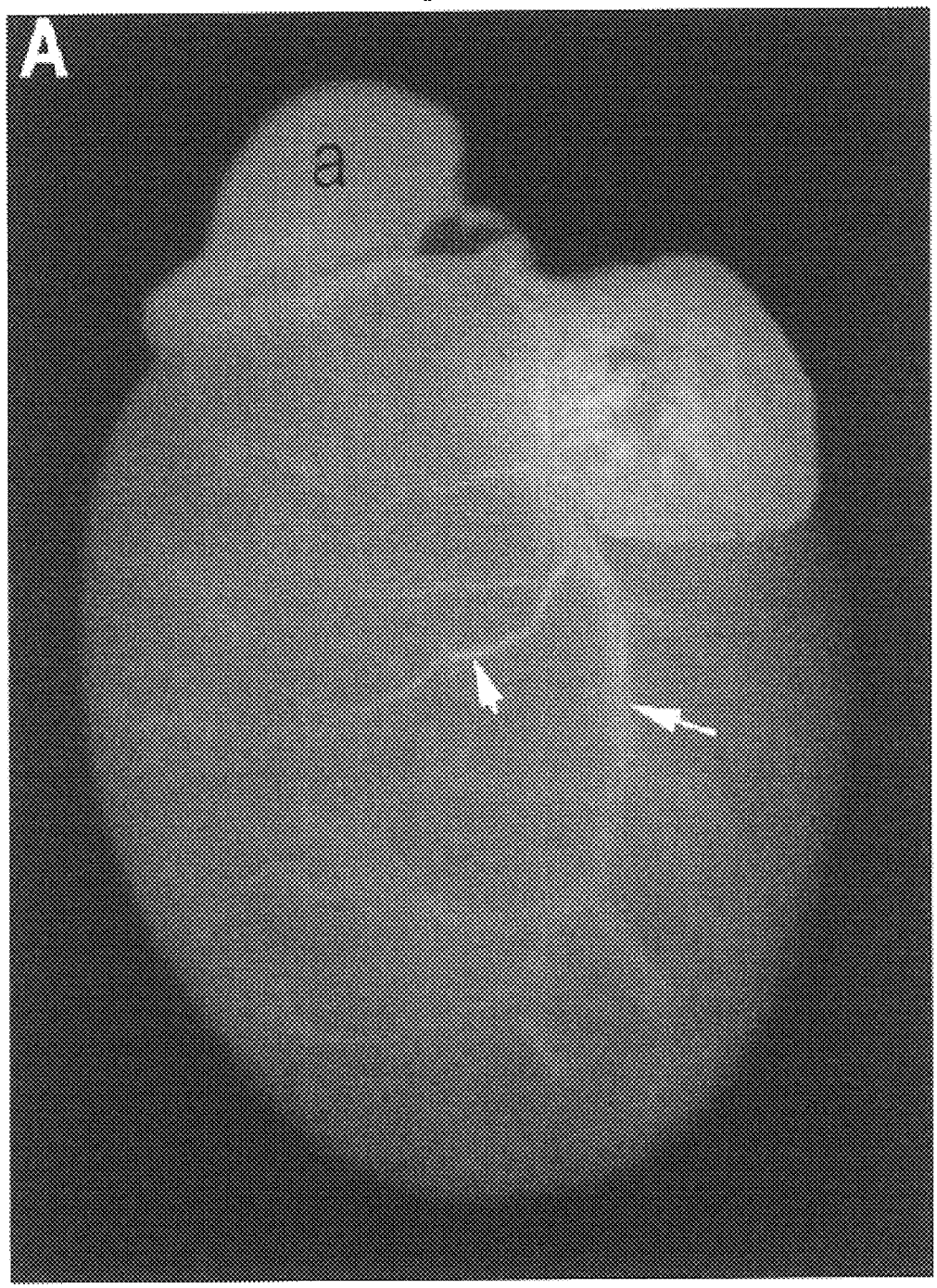
Figure 2B:
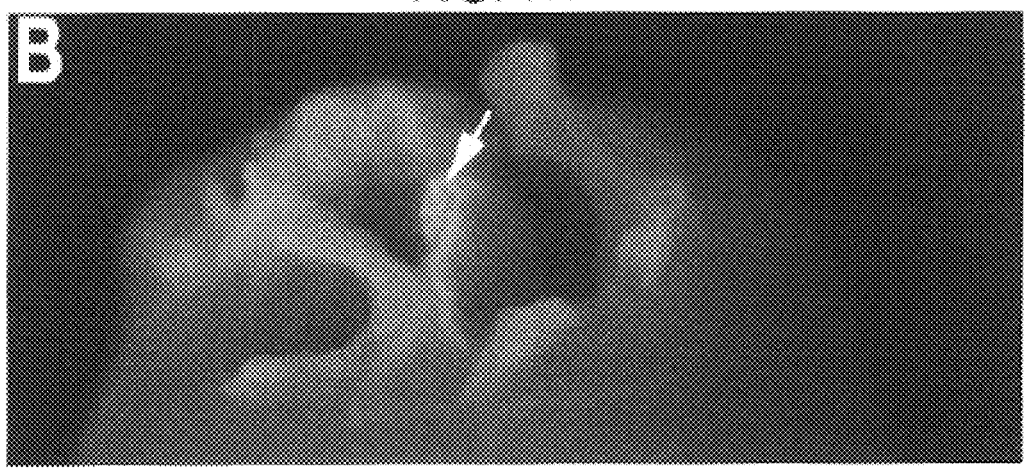
Figure 2C:
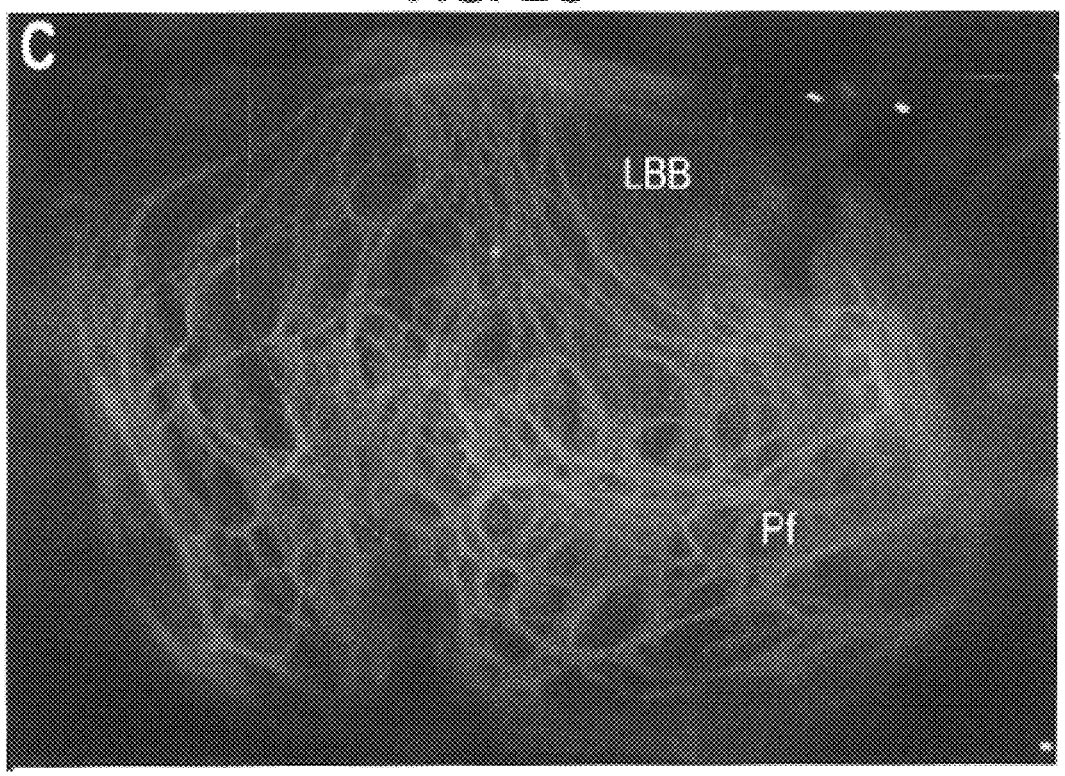
Figure 2D:
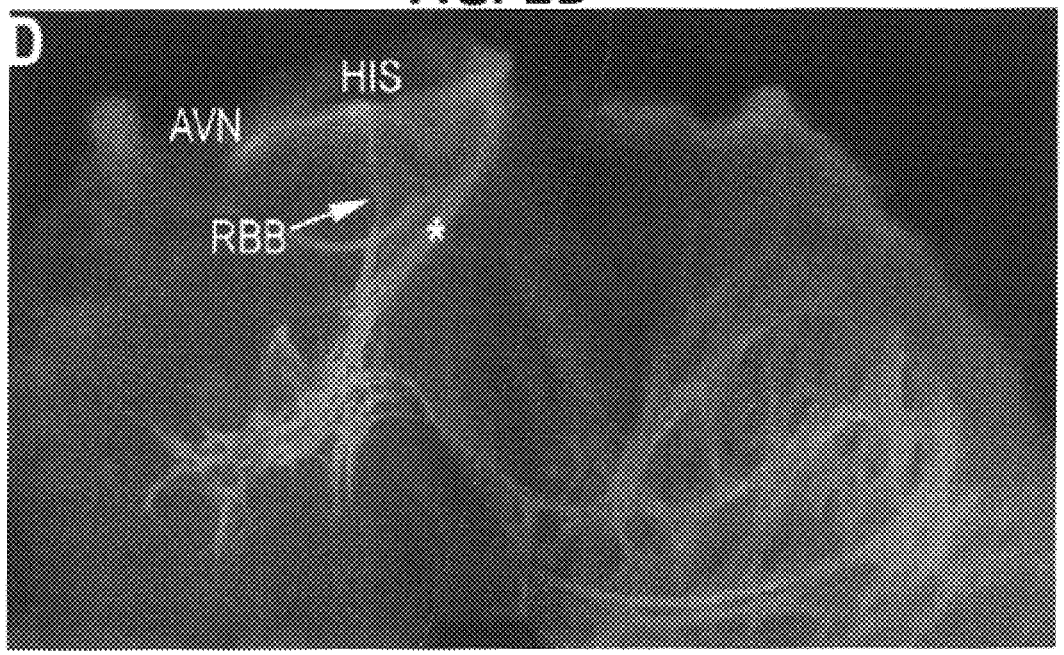

Insertion of the eGFP coding sequence into the Connexin 40 gene locus was achieved by homologous recombination (FIG. 1A). Embryonic stem (ES) cell clones harboring the targeted allele, Cx40KI-eGFP, were identified by Southern blotting (FIG. 1E). Heterozygous mice were obtained and two independent lines were established. The $Cx40^{KIGFP/+}$ mice are viable, fertile and transmit the knock-in allele to the offsprings with a Mendelian frequency Transcription of the knock-in allele was verified by reverse transcriptase-polymerase chain reaction (RT-PCR) (FIG. 1C). Immunofluorescence with an anti-Cx40 antibody was performed to confirm the co-expression of eGFP and Cx40 in the same cells (FIG. 1D,E). In adult $Cx40^{KIGFP/+}$ mice, eGFP fluorescent is observed in the endothelial cells of the main blood vessels (not shown) and in cardiac coronaries (FIG. 2A). In the heart, eGFP is detected in the right and left atria (FIG. 2A). Sections of atria shows that all atrial cardiomyocytes are OFF positive (FIG. 1F). After removal of the atria, the common His bundle is easily identified by a strong expression of GFP at the top of the interventricular septum (FIG. 2B). The AVN is visible at the extremity of the common His bundle just beside the tricuspid valve in the right ventricle (FIG. 2D) Ventricular cavities were cut on one side and then opened to observe green fluorescent in the entire ventricular CCS present on the internal surfaces of each ventricle (FIG. 2C, D) On the left side of the septum, the left bundle branch (LBB) is composed by an important ramification of fibers coming from the His bundle and running parallel toward the apex of the heart (FIG. 2C). The number of fibers composing the LBB differed from one animal to another but it was always distributed over the left septal surface. From the middle of the septum side, the LBB ramifies into a dense network of Purkinje fibers (P0, which cover a large part of the internal ventricular cavity. As it was observed in big mammals (Anderson et al., 1975), the size of the proximal branching of the LBB is thinner in comparison to the Pf. Moreover, in contrast to the fibers of the LBB parallel organized, the Pf formed a web of mixed up fibers (FIG. 2C). The picture of the CCS given in the right ventricle differs from the left side by different anatomic details (FIG. 2D) Firstly, the RBB includes only one branch reliable from the common His bundle and descending along the right septal surface. Secondly, the RBB ramifies at about halfway toward the apex and from this important branching only few fibers are connected to the network of Pf principally localized on the surface of the right ventricular free wall. These data show for the first time the entire image of the murine cardiac conduction system. It is noteworthy that the discrepancies observed in the left and right bundle branches, correspond point to point to the first description of cardiac conduction system in human by Tawara et al in 1906 and more recently by Anderson et al. Even if the murine Pf are not distinguishable by fibrosis like in human, these results show that the arrangement of the entire CCS is identical in both species.

Figure 2E:
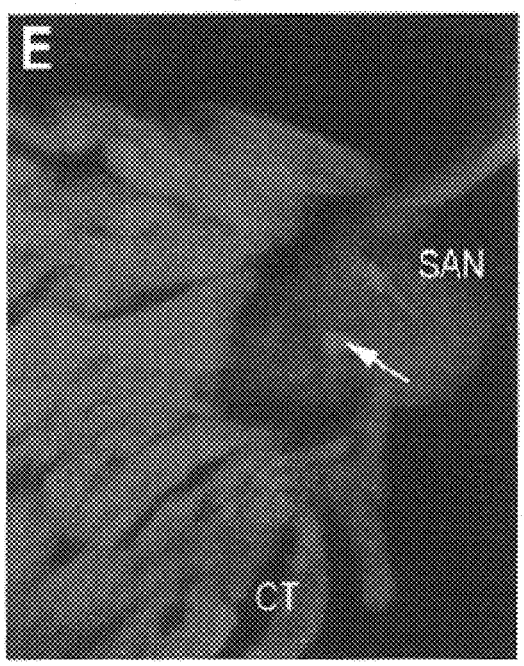
Figure 2F:
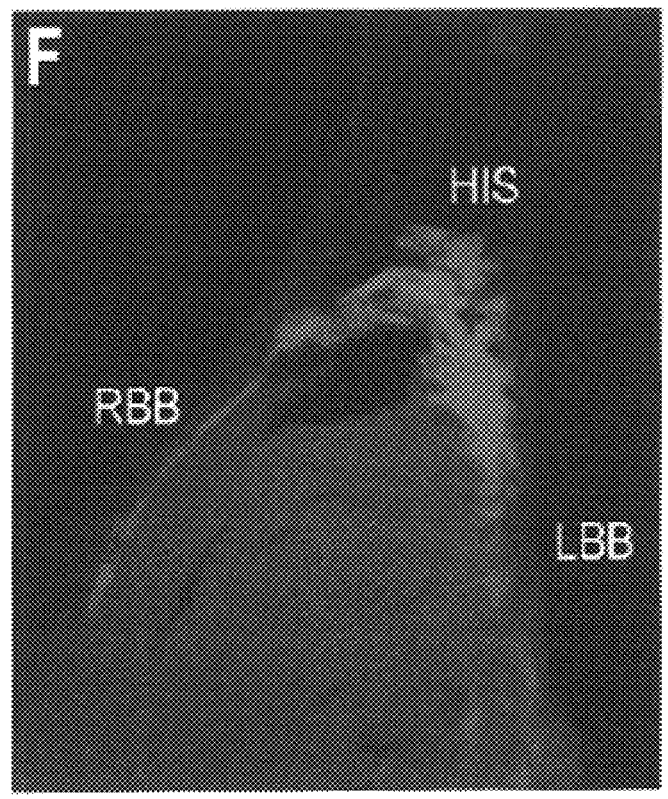
Figure 2G:
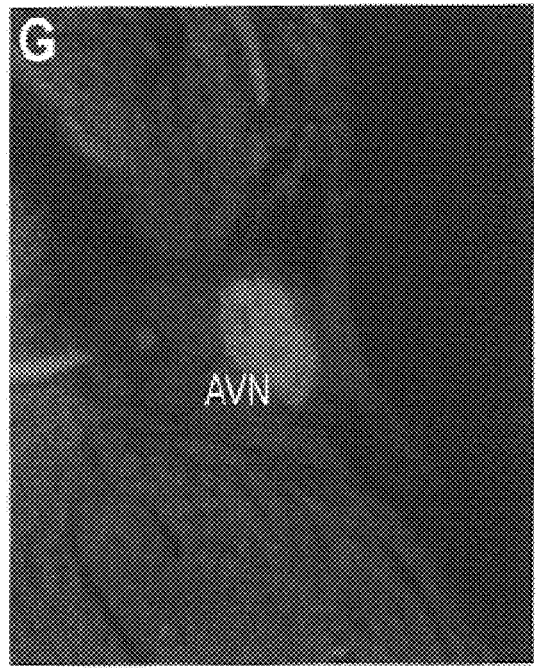
Figure 2H:
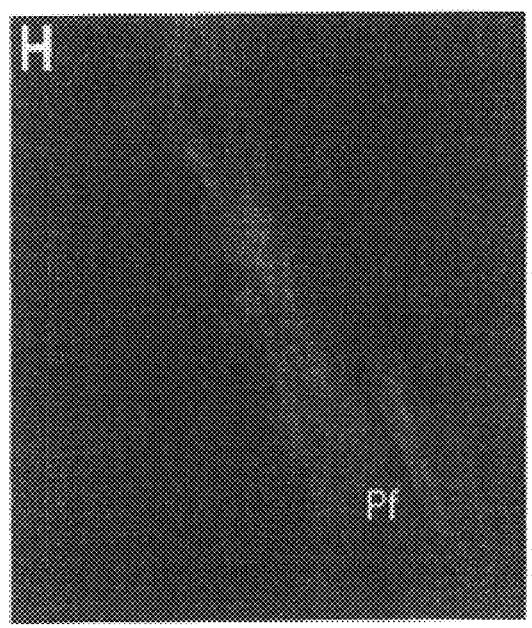

Histological analyses were performed to explore in more details the different components of the CCS. As it was defined before, there is a distinction between nodal cells forming the SAN and the AVN that present specific features of pacemaker and that are defined as slow conductive cells which do expressed the Cx45 and not the Cx40 marker (Boyett et al., 2000; Coppen et al., 1999; Verheijck et al., 2001). The Cx40 is considered by its distribution and by its conductance properties as a marker for rapid conduction cells like the Purkinje cells (Gros et al., 1994). In the SAN, no GFP fluorescent has been observed in the nodal cells confirming the results that the Cx40 gene is not expressed in these cells (Verheijck et al., 2001) (FIG. 2E). The only GFP positive cells detected in this region correspond to the endothelial cell of the nodal artery (FIG. 2K, arrowhead). However, GFP fluorescent is present in the surrounding crista terminalis of the right atrium. In consequence, the SAN represents the only negative structure of the atria in the $Cx40^{GFP/+}$ mice. The AVN is in continuity of the His bundle and it is positive for GFP (FIG. 2F). However, the compact node presents an heterogeneity of cells expressing GFP suggesting that Cx40 is not expressed in the totality of the nodal cells. Using a Cx40 antibody, only few positive cells can be positively detected in the center of the node. The wider expression of GFP in the AVN can be explained by the higher sensitivity of GFP detection compared to immunofluorescence with an anti-Cx40 antibody. Saggital sections of the interventricular septum allow the visualization of the HIS bundle, the LBB and RBB which all are GFP positive (FIG. 2G) The cardiac conduction system ends by the presence of numerous Pf at the endocardial surface of ventricular walls (FIG. 2G). These histological analyses confirmed that the murine Pf are exclusively localized at subendocardial position, we do not observe penetrating GFP+ cells in the ventricular free wall. The high level of GFP in the Purkinje cells forming the His and Purkinje system is related to the rapid conduction observed in these cells. Indeed, the presence of a large number of gap junctions have been observed between these cells (James and Sherf, 1971).

To characterize electrical features of these cells, we performed action potentials (APs) recordings from ventricular myocytes identified as working GFP–, or conductive GFP+. APs of GFP+ cells from the RBB and the left web, display a distinct profile in comparison to the GFP– working cardiomyocyte that is triangulated and with no plateau (FIGS. 3A, 3B, 3C). The AP profile of a GFP+ conductive cardiomyocyte is characterized by a rapid phase 1 repolarization and a very distinct plateau in phase 2. The analysis of AP parameters shows that the action potential duration is significantly more prolonged in conductive cardiomyocytes than in working myocardium (table 1; APD70 and 90). These results are in accordance with those obtained by Anumonwo et al. (2001), indicating that GFP+ cardiomyocytes are representative of the pool of conductive cardiomyocytes. The specificity of an AF profile is due to the heterogeneous distribution of ion channels in the cardiomyocytes. Comparison of ionic channel subunits expression in canine Pf and ventricular myocytes has demonstrated a different composition of these channels in both cell type in accordance with their proper ionic properties (Han et al., 2002).

Figure 4A:
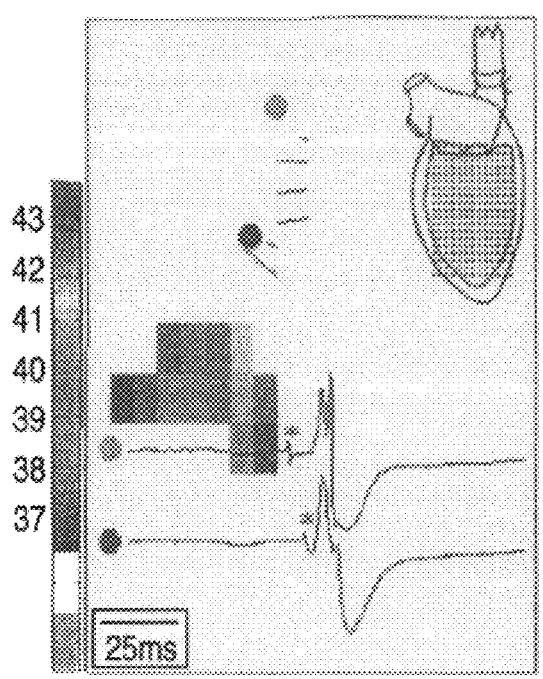
Figure 4B:
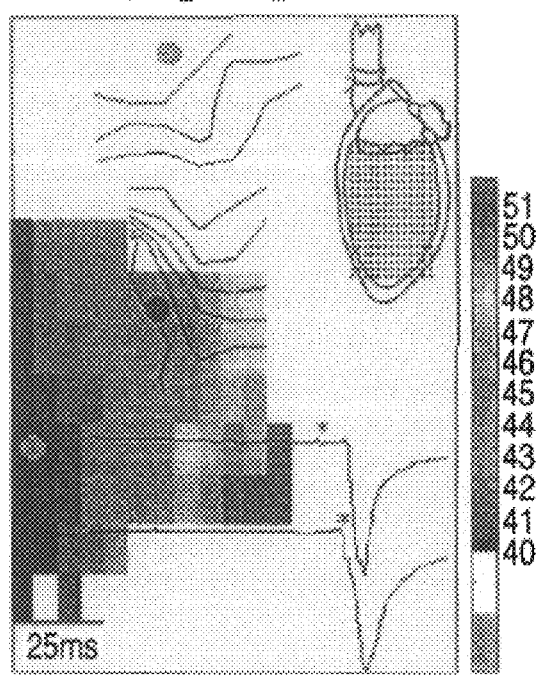
Figure 4C:
Figure 4D:
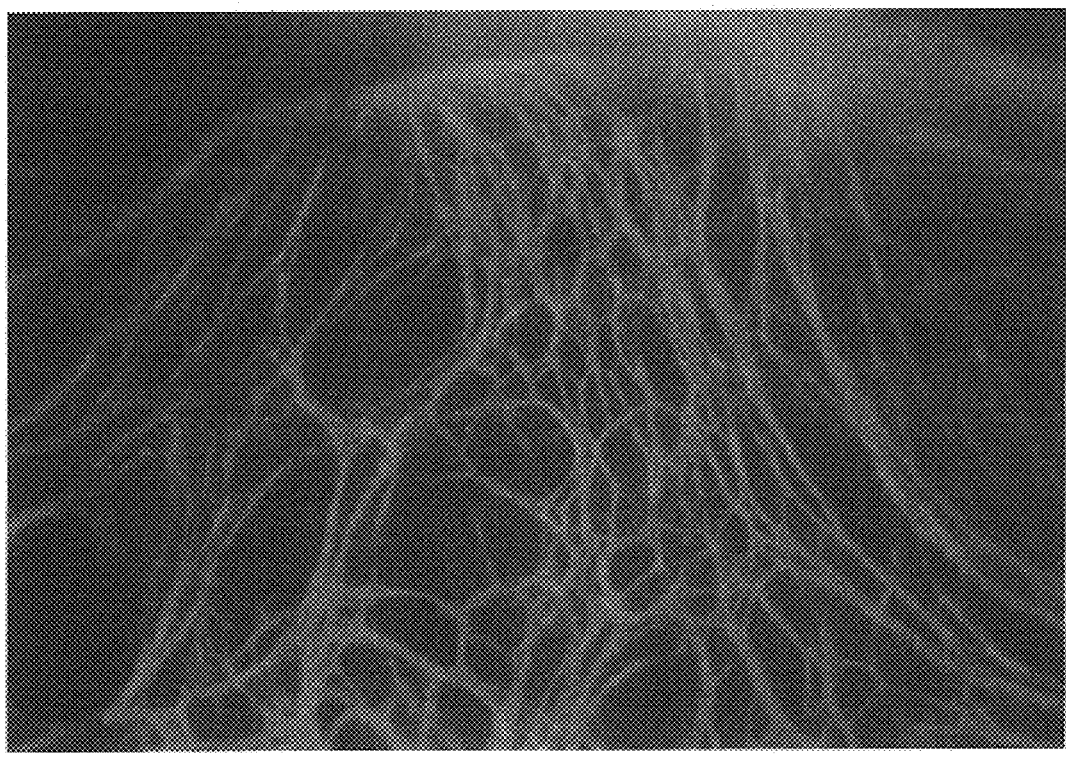

Moreover, we have measured the electrical activation maps of each BB under sinus rhythm. After removal of the left and right ventricular free wall, a microelectrodes grid was applied on the left or right septal wall to measure the specific bundle electrical activity maps. Typical example of left septal activation pattern shows a wide distribution of activated electrodes on the left septal width from base to apex (FIG. 4A). The electrical activation map recorded on the left septum matches perfectly with the large repartition of fibers of the LBB revealed by the GFP expression (FIG. 4C). The right septal activation map is characterized by a thin pattern of activation that is compatible with the compact structure of the RBB seen by GFP (FIG. 4B, D). Moreover, ECGs of heterozygous mice KI Cx40/GFP have been analyzed and were not significantly different from control animals (not shown). These data indicate that the expression of eGFP in the CCS does not impaired the electrical propagation and prove that this mouse model can be used as reference for normal cardiac electrophysiological analyses.

The development of transgenic technology in the mouse has allowed the establishment of murine models for genetic cardiac diseases such as long QT syndrome and hypertrophic cardiomyopathies (London et al., 1998; Reddy et al. 1996). Also, several mouse mutants already exist with defects in ionic channels composition and they are very helpful in the understanding of the electrophysiological mechanisms underlying arrhythmias (Baker et al., 2000; Nuyens et al., 2001; Papadatos et al., 2002). Moreover, a number of conduction defects have been identified in knock-out mice for the Cx40 gene or the transcription factor HF-1b (Kirchhoff et al., 1998; Nguyen-Tran et al., 2000; Simon et al., 1998). If electrophysiological recordings have been performed in the whole animal or on isolated working cardiomyocytes, none of these mutants were examined for their direct effect on the CCS. By intercrossing the $Cx40^{GFP+}$ mice with other mouse mutants, this model will be helpful to directly and precisely analyze defects of the conductive cardiomyocytes. The mouse model is not the more appropriate model to study arrhythmias because a number of discrepancies exist between the mouse and human like the heart size, the heart beats and other electrophysiological parameters (Baker et al. 2000). This explains why larger mammals like rabbit or dog are usually used to study the CCS and its physiopathology. Nevertheless, the mouse represents the model of choice for transgenic technology and ethical reasons. Exploring the fact that a perfect conservation has existed during evolution, in the structure of the CCS in both species, a better understanding of the basic mechanisms underlying these diseases in the mouse will opened the development of new curative therapies.

In conclusion, the KI Cx40/GFP mice represent a powerful and unique model to investigate the molecular and physiological mechanisms implicated the differentiation of the cardiac conduction system.

REFERENCES

Anderson, R H, Becker, A. E., Brechenmacher, C., Davies, M. J. and Rossi, I. (1975). The human atrioventricular junctional area. A morphological study of the A-V node and bundle. *Eur J Cardiol* 3, 11-25.

Anumonwo, J. M., Tallini, Y. N., Vetter, F. J. and Jalife, J., (2001). Action potential characteristics and arrhythmogenic properties of the cardiac conduction system of the murine heart. *Circ Res* 89, 329-35.

Baker, L. C., London, B., Choi, B. R., Koren, G. and Salama, G. (2000). Enhanced dispersion of repolarization and refractoriness in transgenic mouse hearts promotes reentrant ventricular tachycardia. *Circ Res* 86, 396-407.

Bevilacqua, L. M., Simon, A. M, Maguire, C. T., Gehrmann, J., Wakimoto, H., Paul, D. L. and Berul, C. I. (2000). A targeted disruption in connexin40 leads to distinct atrioventricular conduction defects. *J Interv Card Electrophysiol* 4, 459-67.

Boyett, M. R., Honjo, H. and Kodama, I. (2000). The sinoatrial node, a heterogeneous pacemaker structure. *Cardiovasc Res* 47, 658-87.

Coppen, S. R. and Severs, N. J. (2002). Diversity of connexin expression patterns in the atrioventricular node: vestigial consequence or functional specialization? *J Cardiovasc Electrophysiol* 13, 625-6.

Coppen, S. R., Severs, N. J. and Gourdie, R. G. (1999). Connexin45 (alpha 6) expression delineates an extended conduction system in the embryonic and mature rodent heart. *Dev Genet* 24, 82-90.

Davies, M. J., Anderson, R. H. and Becker, A. E. (1983). Anatomy of the conduction tissues. In *The conduction system of the heart*, pp. 9-70. London: Butterworth & Co.

Delorme, B., Dahl, E., Jarry-Guichard, T., Briand, J. P., Willecke, K., Gros, D. and Theveniau-Ruissy, M. (1997). Expression pattern of connexin gene products at the early developmental stages of the mouse cardiovascular system. *Circ Res* 81, 423-37.

Delorme, B., Dahl, F., Jarry-Guichard, T., Marics, I., Briand, J. P., Willecke, K., Gros, D. and Theveniau-Ruissy, M. (1995). Developmental regulation of connexin40 gene expression in mouse heart correlates with the differentiation of the conduction system. *Dev Dyn* 204, 358-71.

Dorman, T., Breslow, M. J. Pronovost, P. J., Rock, P. and Rosenfeld, B. A. (2000). Bundle-branch block as a risk factor in noncardiac surgery. *Arch Intern Med* 160, 1149-52.

Gros, D., Jarry-Guichard, T., Ten Velde, I., de Maziere, A., van Kempen. M. J., Davoust, J., Briand, J. P., Moorman, A. F. and Jongsma. H. J. (1994). Restricted distribution of connexin40, a gap junctional protein, in mammalian heart. *Circ Res* 74, 839-51.

Gros, D. B. and Jongsma, H 1 (1996). Connexins in mammalian heart function. *Bioessays* 18, 719-30.

Hadjantonakis, A. K., Macmaster, S. and Nagy, A. (2002). Embryonic stem cells and mice expressing different GFP variants for multiple non-invasive reporter usage within a single animal. *BMC Biotechnol* 2, 11.

Haissaguerre-. M., Shah, D. C., Jais, P., Shoda, M., Kautzner, J., Arentz, T., Kalushe, D., Kadish, A., Griffith, M., Gaita, F. et al. (2002). Role of Purkinje conducting system in triggering of idiopathic ventricular fibrillation. *Lancet* 359, 677-8.

Han, W., Bao, W., Wang. Z. and Nattel, S. (2002). Comparison of ion-channel subunit expression in canine cardiac Purkinje fibers and ventricular muscle. *Circ. Res* 91, 790-7.

Hennemann, H., Schwarz, H. J. and Willecke. K. (1992). Characterization of gap junction genes expressed in F9 embryonic carcinoma cells: molecular cloning of mouse connexin31 and −45 eDNAs. *Eur J Cell Biol* 57, 51-8.

James, T. N. and Sherf, L. (1971). Fine structure of the His bundle. *Circulation* 44, 9-28.

Kirchhoff, S., Nelles, E., Hagendorff, A., Kruger, 0., Traub, 0. and Willecke, K. (1998). Reduced cardiac conduction velocity and predisposition to arrhythmias in connexin40-deficient mice *Curr Biol* 8, 299-302.

London, B., Jeron, A., Zhou, J., Buckett, P., Han, X., Mitchell, G. F and Koren, G. (1998). Long QT and ventricular arrhythmias in transgenic mice expressing the N terminus and first transmembrane segment of a voltage-gated potassium channel. *Proc Natl Acad Sci USA* 95, 2926-31.

Massing, G. K. and James, T. N. (1976). Anatomical configuration of the His bundle and bundle branches in the human heart. *Circulation* 53, 609-21.

Nagy, A., Rossant, J., Nagy, R., Abramow-Newerly, W. and Roder, J. C. (1993). Derivation of completely cell culture-derived mice from early-passage embryonic stem cells. *Proc Nati Acad Sci USA* 90, 8424-8.

Nguyen-Tran. V. T., Kubalak, S. W., Minamisawa, S., Fiset, C., Wollert, K. C., Brown, A. B., Ruiz-Lozano, P., Barrere-Lemaire, S., Kondo, R., Norman. L. W. et al. (2000). A novel genetic pathway for sudden cardiac death via defects in the transition between ventricular and conduction system cell lineages. *Cell* 102, 671-82.

Nuyens, D., Stengl, M., Dugarmnaa, S., Rossenbacker, T., Compemolle, V., Rudy, Y., Smits, J. F., Flameng, W., Clancy, C. E., Moons, L. et al. (2001). Abrupt rate accelerations or premature beats cause life-threatening arrhythmias in mice with long-QT3 syndrome. *Nat Med* 7, 102 1-7.

Papadatos, G. A., Wallerstein, P. M., Head, C. E., Ratcliff. R., Brady, P. A., Benndorf, K., Saumarez, R. C., Trezise, A. F., Huang, C. L., Vandenberg, J. I. et al. (2002). Slowed conduction and ventricular tachycardia after targeted disruption of the cardiac sodium channel gene Sen5a. *Proc Natl Acad Sci USA* 99, 6210-5.

Reddy, S., Smith, D. B., Rich, M. M. Leferovich, J. M., Reilly, P., Davis, B. M., Tran, K., Rayburn, H., Bronson, R., Cros, D. et al. (1996). Mice lacking the myotonic dystrophy protein kinase develop a late onset progressive myopathy. *Nat Genet* 13, 325-35.

Rentschler, S., Vaidya, U. M., Tamaddon, H., Degenhardt, K., Sassoon, D., Morley, G.

E., Jalife, J. and Fishman. G. I. (2001). Visualization and functional characterization of the developing murine cardiac conduction system. *Development* 128, 1785-92.

Roberts, R and Brugada, R. (2003). Genetics and arrhythmias. *Annu Rev Med* 54, 257-67.

Schram. G., Pourrier, M., Melnyk, P. and Nattel, S. (2002). Differential distribution of cardiac ion channel expression as a basis for regional specialization in electrical function. *Circ Res* 90, 939-50.

Simon, A. M., Goodenough, D. A. and Paul, D. L. (1998). Mice lacking connexin40 have cardiac conduction abnormalities characteristic of atrioventricular block and bundle brunch block. *Curr Biol* 8, 295-8.

Tamaddon, H. S., Vaidya, D., Simon, A. M. Paul, D. L., Jalife, J. and Morley, G. E. (2000). High-resolution optical mapping of the right bundle branch in connexin40 knockout mice reveals slow conduction in the specialized conduction system. *Circ Res* 87, 929-36.

Tawara, S. (1906). *Das Reisleitungssystem des Saugetierherzcns*. Gustav Fisher Jena.

van Rijen, H. V., van Veen, T. A., van Kempen, M. J., Wilms-Schopman, F. J., Potse, M., Krueger, O., Willecke, K., Opthof, T., Jongsma, H. J. and de Bakker, J. M. (2001). Impaired conduction in the bundle branches of mouse hearts lacking the gap junction protein connexin40. *Circulation* 103, 1591-8.

Potse, M., Linnenbank, A. C. and Grimbergen, CA (2002). Software design for analysis of multichannel intracardial and body surface electrocardiograms. *Comput Methods Programs Biomed* 69, 225-36.

van Veen, T. A., van Rijen, H. V., Wiegerinck, R. F., Opthof, T. Colbert, M. C., Clement, S., de Bakker, J. M. and Jongsma, H. J. (2002). Remodeling of gap junctions in mouse hearts hypertrophied by forced retinoic acid signaling. *J Mol Cell Cardiol* 34, 1411-23.

Verheijck, E. E., van Kempen, M. J., Veereschild, M., Lurvink, I., Jongsma, H. J. and Bouman, L. N. (2001). Electrophysiological features of the mouse sinoatrial node in relation to connexin distribution. *Cardiovasc Res* 52, 40-50.

Viragh, S. and Challice, C. E. (1977a). The development of the conduction system in the mouse embryo heart. I. The first embryonic A-V conduction pathway. *Dev Biol* 56, 382-96.

Viragh, S. and Challice, C. E. (1977b). The development of the conduction system in the mouse embryo heart. II. Histogenesis of the atrio-ventricular node and bundle. *Dev Biol* 56,397-411.

Zipes, D. P. and Wellens, H. J. (1998). Sudden cardiac death. *Circulation* 98, 2334-51.

The invention claimed is:

1. A transgenic mouse whose genome comprises a fluorescence reporter gene inserted into the connexin 40 (Cx40) gene such that the reporter gene is in operable linkage with the endogenous Cx40 promoter and the Cx40 gene leading to co-expression and co-localization of the reporter protein and a functional Cx40 protein and wherein said reporter gene is expressed in the atrio-ventricular node (AVN), His bundle, bundle branches, and Purkinje fibers of the cardiac conduction system (CCS).

2. The transgenic mouse of claim 1, wherein the mouse is homozygous for said fluorescence reporter gene.

3. The transgenic mouse according to claim 1, wherein said reporter gene is an eGFP gene.

4. A mouse offspring resulting from a mating with the mouse according to claim 3, wherein said mouse offspring is homozygous for said eGFP gene.

* * * * *

SEQUENCE LISTING

<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agagcaaata acagtgggca gttga                                          25

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
accaggctga atggtatcg                                                 19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agaagtcgtg ctgcttcatg                                                20